US012624332B2

(12) United States Patent
Bartake et al.

(10) Patent No.: US 12,624,332 B2
(45) Date of Patent: May 12, 2026

(54) AUTOMATED INTEGRATED CONTINUOUS SYSTEM AND BIOPROCESS FOR PRODUCING THERAPEUTIC PROTEIN

(71) Applicant: ENZENE BIOSCIENCES LIMITED, Pune Maharashtra (IN)

(72) Inventors: Hrishikesh Bartake, Pune Maharashtra (IN); Himanshu Gadgil, Pune Maharashtra (IN); Abir Banerjee, Pune Maharashtra (IN); Harshita Londhe, Pune Maharashtra (IN); Abijar Bhori, Pune Maharashtra (IN); Abhijit Butti, Pune Maharashtra (IN); Samir Varma, Pune Maharashtra (IN); Rohan Godse, Pune Maharashtra (IN); Veerendra Reddy, Pune Maharashtra (IN)

(73) Assignee: ENZENE BIOSCIENCES LIMITED, Pune Maharashtra (IN)

(*) Notice: Subject to any disclaimer, the term of this patent is extended or adjusted under 35 U.S.C. 154(b) by 1050 days.

(21) Appl. No.: 17/425,471

(22) PCT Filed: Apr. 1, 2019

(86) PCT No.: PCT/IB2019/052654
§ 371 (c)(1),
(2) Date: Jul. 23, 2021

(87) PCT Pub. No.: WO2020/152509
PCT Pub. Date: Jul. 30, 2020

(65) Prior Publication Data
US 2022/0090001 A1 Mar. 24, 2022

(30) Foreign Application Priority Data
Jan. 25, 2019 (IN) ............................. 201921003147

(51) Int. Cl.
*C12M 1/00* (2006.01)
*C12M 1/26* (2006.01)
(Continued)

(52) U.S. Cl.
CPC ............ *C12M 47/12* (2013.01); *C12M 29/04* (2013.01); *C12M 33/14* (2013.01); *C12M 41/48* (2013.01); *C12P 21/00* (2013.01)

(58) Field of Classification Search
CPC ...... C12M 47/12; C12M 29/04; C12M 33/14; C12M 41/48; C12M 37/00; C12M 41/26; C12M 41/32; C12M 41/44; C12P 21/00
(Continued)

(56) References Cited

U.S. PATENT DOCUMENTS

2005/0272146 A1* 12/2005 Hodge ................... B01F 35/513
435/289.1
2011/0060463 A1* 3/2011 Selker ................ G05B 23/0221
700/266
(Continued)

FOREIGN PATENT DOCUMENTS

WO 2014137903 A2 9/2014

OTHER PUBLICATIONS

International Search Report and Written Opinion issued in corresponding Application PCT/IB2019/052654 on Sep. 23, 2019.
Rahul Godawat et al, "End-to-end integrated fully continuous production of recombinant monoclonal antibodies", Journal of Biotechnology, Jun. 1, 2015 (Jun. 1, 2015).
Fabian Steinebach et al, "Continuous counter-current chromatography for capture and polishing steps in biopharmaceutical production", Biotechnology Journal, vol. 11, No. 9, Sep. 1, 2016 (Sep. 1, 2016), p. 1126-1141.
(Continued)

*Primary Examiner* — Charles Capozzi
*Assistant Examiner* — Jacqueline Brazin
(74) *Attorney, Agent, or Firm* — Calderon Safran & Wright P.C.; David S. Safran

(57) ABSTRACT

The present invention relates to an automated integrated continuous bioprocess system and bioprocess that are capable of continuously producing therapeutic protein in an uninterrupted manner and scalable from laboratory to manufacturing scale. The present invention provides an automated integrated continuous bioprocess system and biopro-
(Continued)

cess for producing therapeutic protein, in which the system and process is controlled with one or more control system selected from supervisory control and data acquisition (SCADA) control system (110), proportional integral derivative (PID), programmable logic circuit (PLC), industrial PC (IPC), distributed control system (DCS), message relaying system and automated UPLC/HPLC sampling for online testing to run the system and process and in an uninterrupted manner and continuously produce therapeutic protein.

7 Claims, 7 Drawing Sheets

(51) Int. Cl.
  *C12M 1/36* (2006.01)
  *C12P 21/00* (2006.01)

(58) Field of Classification Search
  USPC ...................................................... 435/283.1
  See application file for complete search history.

(56) References Cited

U.S. PATENT DOCUMENTS

| | | | |
|---|---|---|---|
| 2012/0241045 A1* | 9/2012 | Aouad | B01F 35/1453 |
| | | | 141/83 |
| 2014/0255994 A1* | 9/2014 | Konstantinov | C12N 9/2402 |
| | | | 435/69.6 |
| 2015/0353896 A1 | 12/2015 | Bruninghaus et al. | |
| 2017/0107476 A1* | 4/2017 | Polley | G01N 30/8662 |

OTHER PUBLICATIONS

Daniel J. Karst et al, "Process performance and product quality in an integrated continuous antibody production process : Integrated Continuous Antibody Production Process", Biotechnology and Bioengineering, vol. 114, No. 2, Feb. 1, 2017 (Feb. 1, 2017), p. 298-307.

James Pollock et al, "Integrated continuous bioprocessing: Economic, operational, and environmental feasibility for clinical and commercial antibody manufacture", Biotechnology Progress, vol. 33, No. 4, Jun. 2, 2017 (Jun. 2, 2017), p. 854-866.

* cited by examiner

AUTOMATED INTEGRATED CONTINUOUS SYSTEM AND BIOPROCESS FOR PRODUCING THERAPEUTIC PROTEIN

FIELD OF THE INVENTION

The present invention generally relates to system for continuous bioprocess for producing therapeutic protein. Specifically, the present invention relates to an automated integrated continuous bioprocess system and bioprocess that are capable of continuously producing therapeutic protein and scalable from laboratory to manufacturing scale.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Identification of significance of therapeutic protein has led to new revolution in biopharmaceutical industry. However, production of therapeutic protein commonly observes their charged isoforms which largely interfere in the isolation and purification processes that are required to attain high yields and quality in the product.

Conventionally, therapeutic proteins are manufactured by biopharmaceutical companies using batch processing, in which unit operations are performed and completed before the process stream moves to the next step. Recently, biopharmaceutical companies are following continuous bioprocess for manufacturing of the therapeutic protein. In continuous bio-processing, the processed products are moved to the next step as each unit process is completed. Continuous bio-processing has gained a large amount of interest because of various advantages like steady-state operation, small equipment size, high volumetric productivity, streamlined process flow, low cycle time and reduced capital cost.

Various approaches have been attempted in the existing art for manufacturing therapeutic protein using continuous bio-process methods. However, such existing continuous bio-processes are pseudo continuous process containing standalone units, each performing their function. In such systems each unit operation has limited communication between the individual system parameters and operate mostly in isolation. Further, the current continuous processes mostly involve offline chromatography analysis with limited or no feedback to the ongoing process. As biopharmaceutical companies continue to grow, there is an unmet need to provide an automated integrated bio-process and system for manufacturing therapeutic protein that can be scalable from laboratory to manufacturing scale.

OBJECTS OF THE INVENTION

An object of the present invention is to provide an automated integrated continuous bioprocess system for producing therapeutic protein.

Another object of the present invention is to provide an automated integrated continuous bioprocess for producing therapeutic protein using a control system with communication and programmable control function to regulate the entire process parameters using a master controller.

Another object of the present invention is to provide an automated integrated continuous bioprocess for producing therapeutic protein which can be carried out in continuous and uninterrupted manner.

SUMMARY OF THE INVENTION

The present invention in some of the aspects relate to an automated integrated continuous bioprocess system for producing therapeutic protein in an uninterrupted manner using a control system with communication and programmable control function to regulate the entire process parameters using a master controller In an aspect the present invention provides an automated integrated continuous bioprocess system for producing a therapeutic protein comprising:

a bioreactor (103) to culture mammalian cells capable of producing the therapeutic protein in the culture medium, the bioreactor (103) enabled with alternating tangential flow (ATF) filter (109) to collect a harvest comprising the protein secreted into the culture medium;

a first chromatography system (119) connected to the ATF filtration system (109) of the bioreactor (103) without any intermediate hold vessel to purify the harvested recombinant therapeutic protein and provide protein A eluate;

a viral inactivation system (126) including a viral inactivation vessel (128) connected to the a first chromatography system (119) to collect the protein A eluate and inactivate viruses that may be present in the eluate, and the viral inactivation vessel (128) configured to automatically adjust pH of the protein A eluate;

a collection vessel (136) connected with the viral inactivation vessel (128) through one or more filters to receive the virus inactivated, neutralized, and filtered protein A eluate, wherein said one or more filter(s) (224) and (226) are configured to remove impurities in the form of precipitates from the neutralized protein A eluate received from the viral inactivation vessel;

a second chromatography system (137) connected with the collection vessel (136) to receive the filtered protein A eluate from the collection vessel (136) and provide further purified protein.

In an aspect, the present invention provides the automated integrated continuous bioprocess system optionally further comprising an additional collection vessel (140) connected to the second chromatography system (137) to receive and store the purified protein which may be optionally further purified using one or more filters (142) and provide further purified therapeutic protein.

In an aspect, the present invention provides the automated integrated continuous bioprocess system further comprising one or more control system selected from supervisory control and data acquisition (SCADA) control system (110); proportional integral derivative (PID) [Not shown]; programmable logic circuit (PLC) (112); industrial PC distributed control system (DCS) [Not shown]; Input-Output Modules or IO Boxes (130) and (132) operably connected with individual systems such as the chromatography system 1 (119); the viral inactivating system (128); the collection vessel (136); the chromatography system 2 (137); and message relaying system [Not shown].

In an aspect, the present invention provides the automated integrated continuous bioprocess system further comprising one or more of solenoid or pneumatic pinch valves (114), and optionally comprising of flow meters, air bubble sensors, pressure sensors and load cell(s) for creating a feedback loop in order to maintain fluid flow between various components of the system, avoid formation of air bubbles and regulate the flow of the liquid.

In an aspect, the present invention provides the automated integrated continuous bioprocess system further comprising surge bag (116) connected with the bioreactor through one of the pinch valve (114).

In an aspect, the present invention provides the automated integrated continuous bioprocess system comprising the viral inactivation vessel (128), one or more pH probe connected to a pH transmitter used for measuring the pH of the protein A eluate, and autotitrator including of PLC and pumps (122) in turn connected to containers (124) holding acid and base used for titration, level sensors to check level of fluid in the vessel, and inline turbidity measuring sensors to measure real time nephelometric turbidity unit (NTU).

In an aspect, the present invention provides the automated integrated continuous bioprocess system wherein each of the filters between viral inactivation vessel and the collecting vessel is between 0.2-0.45 micron filter.

In one aspect, the present invention provides the automated integrated continuous bioprocess system wherein the viral inactivation vessel, the collection vessel and the additional collection vessel are made of glass or stainless steel.

In one aspect, the present invention provides the automated integrated continuous bioprocess system wherein the first chromatography system includes one or more affinity chromatography column(s) and the second chromatography system includes one or more multimodal anion exchange column(s) and one or more cation exchange column(s).

In an aspect, the present invention provides the automated integrated continuous bioprocess system wherein the system further comprises cleaning in place (CIP) system (120) for periodic cleaning of chromatography system inlet, viral inactivation vessel, collection vessel and liquid flow tubings.

In an aspect, the present invention provides the automated integrated continuous bioprocess system wherein the system further includes an automated harvest sampling from bioreactor for cell count and nutrient analysis, and automated sampling at different locations for online chromatography analysis during the continuous bioprocess.

The present invention in some other aspects relate to a continuous bioprocess for producing therapeutic protein in an uninterrupted manner that can be scalable from laboratory to manufacturing scale.

In an aspect, the present invention provides an automated integrated continuous bioprocess for producing therapeutic protein, in which the process is controlled with one or more control system(s) selected from supervisory control and data acquisition (SCADA) control system (110), proportional integral derivative (PID), programmable logic circuit (PLC), industrial PC (IPC), Distributed control system (DCS), and message relaying system, and the process comprises steps of:

(a) culturing mammalian cells capable of producing a therapeutic protein in a liquid culture medium in a bioreactor (103) enabled with alternating tangential flow (ATF) filter (109) and collecting a bleeding harvest comprising protein secreted in the culture medium;

(b) feeding the cell culture harvest comprising the therapeutic protein from the bioreactor (103) into a first chromatography system (119) to provide a protein elute A;

(c) feeding the protein A eluate from the first chromatography system (119) into a viral inactivation vessel (128) and allowing inactivation of viruses and neutralization of the protein A eluate, (d) passing the virus inactivated, and neutralized protein A eluate through one or more filter(s) to remove impurities in the form of any precipitate formed during the viral inactivation and neutralization steps, and collecting a filtered protein A eluate in the collection vessel (136) and;

(e) feeding the filtered protein A eluate to the second chromatography system (137) to provide a purified protein.

In an aspect, the present invention provides the automated integrated continuous bioprocess optionally further comprising storing the purified protein in an additional vessel (140) received from the second chromatography system (137). In an aspect, the present invention provides the automated integrated continuous bioprocess optionally further comprising one or more steps of passing the purified protein through one or more filters (142) to further purify the therapeutic protein.

In an aspect, the present invention provides the automated integrated continuous bioprocess, wherein mammalian cells are cultured in a bioreactor (103), which is a perfusion bioreactor enabled with alternating tangential flow (ATF) technology.

In an aspect, the present invention provides the automated integrated continuous bioprocess, wherein the clarified cell culture harvest is directly fed from bioreactor (103) into the first chromatography system (119) using the first chromatography system pump.

In an aspect, the present invention provides the automated integrated continuous bioprocess, wherein the first chromatography is carried out using one or more affinity chromatography column(s) for purifying the cell culture harvest comprising the therapeutic protein from the bioreactor and providing a protein A elute.

In an aspect, the present invention provides the automated integrated continuous bioprocess, wherein pH of the protein A eluate in the viral inactivation step is adjusted automatically controlled by one or more of proportional-integral-derivative (PID) controller, programmable logic controller (PLC) or industrial computer (IPC) controller.

In an aspect, the present invention provides the automated integrated continuous bioprocess, wherein in the second chromatography step is carried out using one or more multimodal anion exchange column(s), and one or more cation exchange column(s) respectively to provide a purified protein.

In an aspect, the present invention provides the automated integrated continuous bioprocess, wherein the process includes automated sampling for online testing, and cleaning in place using the (CIP) system (120) for periodic cleaning of chromatography systems, tubes and vessels to maintain uninterrupted operation.

In an aspect, the present invention provides the automated integrated continuous bioprocess, wherein the therapeutic protein produced is selected from an antibody, an antibody fragment, a monoclonal antibody, an enzyme, a recombinant protein, an engineered protein, an immunogenic protein, a protein fragment, a peptide, an immunoglobulin or any combination thereof.

Various objects, features, aspects and advantages of the inventive subject matter will become more apparent from the following detailed description of preferred embodiments.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DETAILED DESCRIPTION OF THE INVENTION

Figure 1:
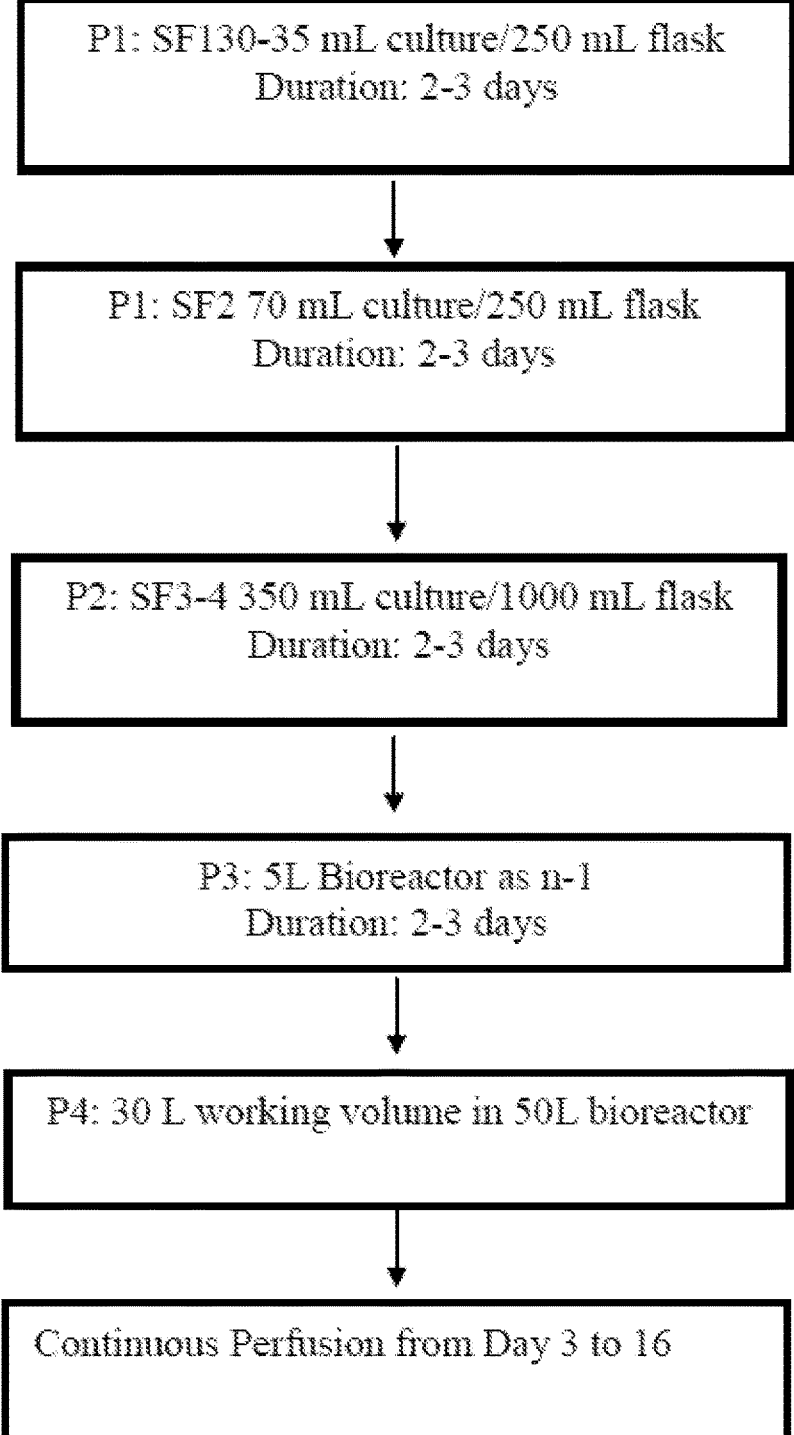
FIG. 1 illustrates an exemplary process flow for upstream process.

The following is a detailed description of embodiments of the disclosure. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context requires otherwise, throughout the specification which follow, the word "comprise" and variations thereof, such as, "comprises" and "comprising" are to be construed in an open, inclusive sense that is as "including, but not limited to."

The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description requirements.

The description that follows, and the embodiments described herein, is provided by way of illustration of an example, or examples, of particular embodiments of the principles and aspects of the present disclosure. These examples are provided for the purposes of explanation, and not of limitation, of those principles and of the disclosure.

It should also be appreciated that the present disclosure can be implemented in numerous ways, including as a system, a method or a device. In this specification, these implementations, or any other form that the invention may take, may be referred to as processes. In general, the order of the steps of the disclosed processes may be altered within the scope of the invention.

The headings and abstract of the invention provided herein are for convenience only and do not interpret the scope or meaning of the embodiments.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Various terms as used herein are shown below. To the extent a term used in a claim is not defined below, it should be given the broadest definition persons in the pertinent art have given that term as reflected in printed publications and issued patents at the time of filing.

The term "continuous bioprocess" as used herein refers to any process having two or more processing steps in a series, wherein the output from an upstream step (unit operation) is transferred to a downstream step (unit operation) continuously till the final chromatography step and wherein it is not necessary for the upstream processing step to run to completion before the next processing step is started. In a continuous process some portion of the target product is always moving through the processing system. Ideally, a continuous process is regulated so that, to the greatest extent possible, every step or unit operation of the continuous process is running at the same time and at substantially the same production rate. In this way, compression of the cycle time is maximized and the shortest possible completion time is achieved.

The term "continuous transfer" refers to a product stream moving from an upstream unit operation to a downstream unit operation, means that the connections or links between the two unit operations are such that the upstream unit operation transfers a product stream (directly or through other components) to the second (downstream) unit operation, and that the downstream unit operation begins before the upstream unit operation runs to completion (that is, the two successive unit operations are processing the product streams flowing into them simultaneously for at least part of the overall process run of which the two unit operations comprise a part).

The term "perfusion cell culture process" as used herein refers to perfusion cultivation which is carried out by continuously feeding fresh medium to the bioreactor and constantly removing the cell-free spent medium while retaining the cells in the reactor; thus, a higher cell density can be obtained in perfusion cultures compared to continuous cultures, as cells are retained within the reactor via a cell retention device. The perfusion rate depends on the demand of cell line, the concentration of nutrients in the feed and the level of toxification.

The term "cell culture medium" refers to all kinds of media which are used in the context of culturing cells. Typically, a cell culture medium comprises amino acids, at least one carbohydrate as an energy source, trace elements, vitamins, salts and possibly additional components (e.g. in order to influence cell growth and/or productivity and/or product quality.

The term "therapeutic protein" means a recombinant protein that has been sufficiently purified or isolated from contaminating proteins, lipids, and nucleic acids present in a liquid culture medium or from a host cell (e.g., from a mammalian, yeast, or bacterial host cell) and biological contaminants (e.g., viral and bacterial contaminants), and can be formulated into a pharmaceutical product for treating or preventing different diseases or disorders. Representative examples of therapeutic protein include, but are not limited to, an antibody, an antibody fragment, a monoclonal antibody, an enzyme, an engineered protein, an immunogenic protein, protein fragment, and an immunoglobulin.

The term "antibody" refers to functional component of serum and is often referred to either as a collection of molecules (antibodies or immunoglobulins, fragments, etc) or as a molecule. An antibody molecule is capable of binding to or reacting with a specific antigenic determinant, which in turn may lead to specific immunological effect or mechanisms.

The term "monoclonal antibody" refers to an antibody produced by a single clone of cells or cell line and consisting of identical antibody molecules.

The term "retention time" as used herein refers to the time in which halve of the quantity of a solute is eluted from the chromatographic system. It is determined by the length of the column and the migration velocity of the solute; which can be in the range of 1-30 minutes.

The term "eluate" as used herein refers to a fluid that is eluted from a chromatography column or chromatographic membrane that contains a detectable amount of a recombinant therapeutic protein.

The present disclosure used various abbreviations, the full form of which are provided herein below:

ATF: Alternating tangential-flow
CV: Column Volume
CEX: Cation exchange (CEX) chromatography
CIP: Cleaning in Place
DO: Dissolved Oxygen
DCS: Distributed control system
HPLC: High Performance Liquid Chromatography
IPC: Industrial PC
min: Minutes
mM Milli Molar
mAU: milli-Absorbance Units
mL: Millilitre
mS/cm: Milli Siemens/centimetre
mA: Milli Amperes
NTU: Nephelometric Turbidity Unit
NaOH: Sodium Hydroxide
PLC: Programmable Logic Circuit
PCC: Periodic Counter Current
PID: proportional-integral-derivative
RV: Reactor Volume
TTL: Transistor-Transistor logic
UV: Ultra Violet
UPLC: Ultra Performance Liquid Chromatography
VI: Viral Inactivation
V: Volts
VCC: Viable Cell Count The present invention in some of the embodiments relate to an automated integrated bioprocess system for continuous production of therapeutic protein in uninterrupted manner controlled by a control system with communication and programmable control function to regulate the entire process parameters using a master controller.

The present invention will now be described more specifically to the following embodiments with reference to the integrated automated system for continuous manufacturing of a therapeutic protein.

Figure 3:
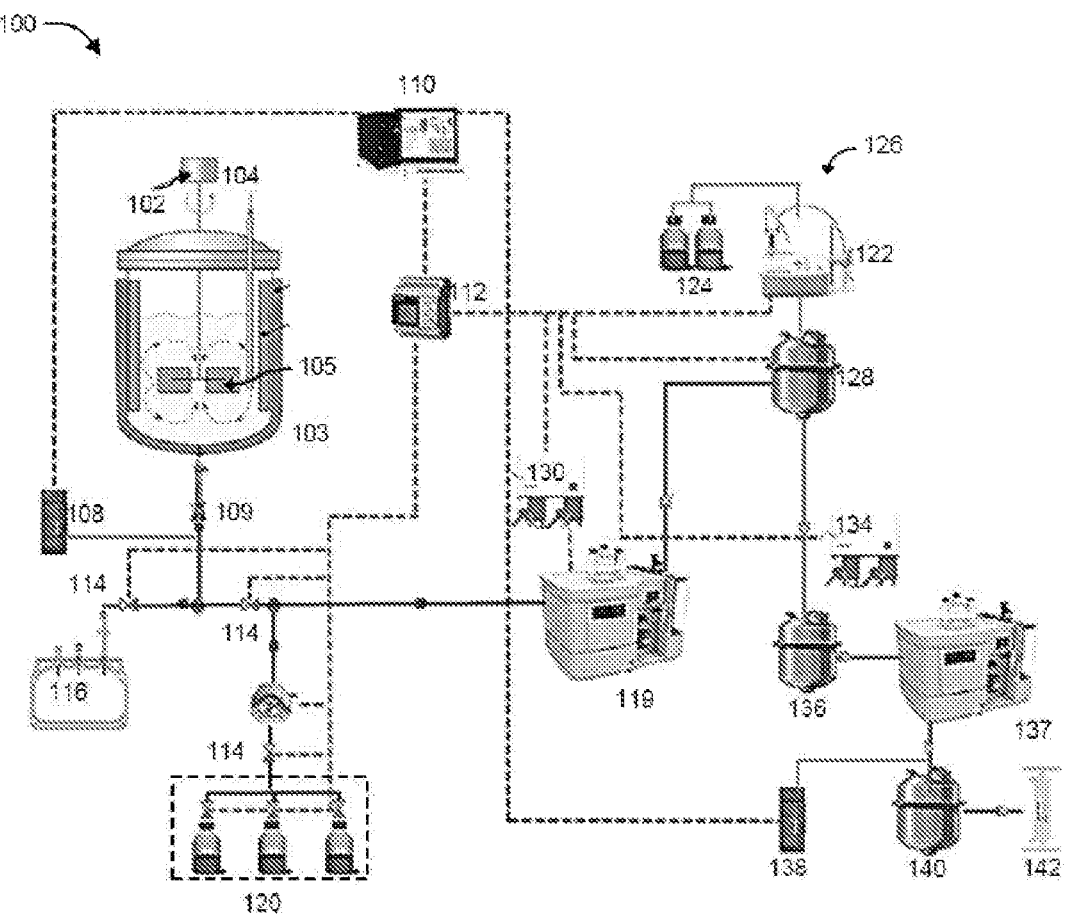
FIG. 3 is a schematic diagram showing the overview of the automated integrated continuous bioprocess system for manufacturing a therapeutic protein.

FIG. 3 illustrates an exemplary automated integrated system for continuous production of therapeutic protein in an uninterrupted manner in accordance with an embodiment of the present invention as disclosed herein below:

The automated integrated system (100) for continuous production of therapeutic protein comprises:

a bioreactor (103) to culture mammalian cells capable of producing the therapeutic protein in the culture medium, the bioreactor (103) mounted with stirrer (102) attached with blades (105), feed inlet (104), and enabled with alternating tangential flow (ATF) perfusion filter (109) to collect a harvest comprising a protein secreted into the culture medium in the bioreactor;

a first chromatography system (119) connected to the ATF filtration system of the bioreactor (103) without any intermediate hold vessel to purify the recombinant therapeutic protein from the culture media produced by the cultured mammalian cell and provide a protein A eluate;

a viral inactivation system (126) including a viral inactivation vessel (128) connected to a first chromatography system (119) to collect the protein A eluate and inactivate the viruses that may be present in the protein A eluate, and the viral inactivation vessel (128) configured to automatically adjust pH of the protein A eluate;

a collection vessel (136) connected with the viral inactivation vessel (128) through one or more filter(s) to receive the neutralized protein A eluate from the viral inactivation vessel (128) upon passing the neutralized protein A eluate through one or more filters to remove impurities in the form of precipitates from the protein A eluate;

a second chromatography system (137) connected with the collection vessel (136) to receive the neutralized and filtered protein A eluate from the collection vessel (136) and provide a purified protein.

In one embodiment, the present invention provides the automated integrated continuous bioprocess system optionally further comprising an additional collection vessel (140) connected to the second chromatography system (137) to receive and store the purified protein which may be optionally further purified using one or more filters (142) and provide further purified therapeutic protein.

In one embodiment, the present invention provides the automated integrated continuous bioprocess system further comprising one or more control system selected from supervisory control and data acquisition (SCADA) control system (110), proportional integral derivative (PID) [Not shown]; programmable logic circuit (PLC), Industrial PC (IPC), distributed control system (DCS) [Not shown]; Input-Output Modules or IO Boxes (130) and (132) operably connected with individual systems including the chromatography system 1 (119); the viral inactivating system (126); the collection vessel (136); the chromatography system 2 (137); and message relaying system [Not shown].

In one embodiment, the present invention provides the automated integrated continuous bioprocess system further comprising one or more of solenoid or pneumatic pinch valves (114), and optionally comprising of flow meters, air bubble sensors, pressure sensors and load cell(s) for creating a feedback loop in order to maintain fluid flow between various components of the system, avoid formation of air bubbles and regulate the flow of the liquid.

In one embodiment, the present invention provides the automated integrated continuous bioprocess system further comprising surge bag (116) connected with the bioreactor through one of the pinch valve (114).

In one embodiment, the present invention provides the automated integrated continuous bioprocess system comprising the viral inactivation system (126) including viral inactivated vessel (128), one or more pH probe connected to a pH transmitter and used for measuring the pH of the protein A eluate and autotitrator consisting of PLC and pumps (122) in turn connected to containers holding acid and base used for titration (124), optionally comprising of level sensors to check level of fluid in the vessel, and inline turbidity measuring sensors to measure real time nephelometric turbidity unit (NTU).

In one embodiment, the present invention provides the automated integrated continuous bioprocess system wherein each of the filters between viral inactivation vessel and the collecting vessel is between 0.2-0.45 micron filter.

In one embodiment, the present invention provides the automated integrated continuous bioprocess system wherein the first chromatography system includes one or more affinity chromatography column(s) and the second chromatography system includes one or more multimodal anion exchange column(s) and one or more cation exchange column(s).

In one embodiment, the present invention provides the automated integrated continuous bioprocess system wherein the viral inactivation vessel, the collection vessel and the additional collection vessel are made of glass or stainless steel.

In one embodiment, the present invention provides the automated integrated continuous bioprocess system wherein the fluid flow is maintained using tubes made of suitable material for example silicone and bioprene. In an embodiment the connectors used are aseptic connectors to reduce system bioburden.

In one embodiment, the present invention provides the automated integrated continuous bioprocess system wherein the system further comprises cleaning in place (CIP) system (120) for periodic cleaning of chromatography systems, viral inactivation vessel, collection vessel, and tubes.

In one embodiment, the present invention provides the automated integrated continuous bioprocess system wherein the system further comprises an automated harvest sampling from bioreactor for cell count and nutrient analysis, and an automated sampling at different locations for online chromatography analysis during the continuous bioprocess.

In one embodiment the automated integrated continuous bioprocess system optionally comprises Ultra Performance Liquid Chromatography (UPLC) systems (108) and (138). In some embodiments the first and second chromatography systems used in the present invention can be high pressure liquid chromatography (HPLC). In another embodiment, the system provides provision to integrate/analysis system using automated sampling system. The controller triggers the HPLC systems to initiate analysis run using suitable one or more digital interfaces selected from but not limiting to Open Platform Communications (OPC), modbus TCP/IP, EtherCAT, Profibus, Profinet, profibus, and industrial ethernet interface.

In an embodiment, the controller regulates multiport electric rotary valve or flow selection valves to regulate the liquid flow. The controller regulates precision pump to start and opens bioreactor sampling port valve. Programmed amount of fluid is collected and for the HPLC system to perform the analysis. HPLC system completes analysis based on set program. HPLC system sends analysis data to the SCADA system.

In another, embodiment, the master controller consisting of IPC with SCADA software controls visualization of the data, monitoring, and as historian of the process parameters. Master controller is connected with individual systems such as the bioreactor, the first chromatography system, the second chromatography system and the virus inactivation system using one or more of digital interfaces selected from but not limiting to OPC, modbus TCP/IP, EtherCAT, profinet, profibus, or industrial Ethernet.

Figure 4:
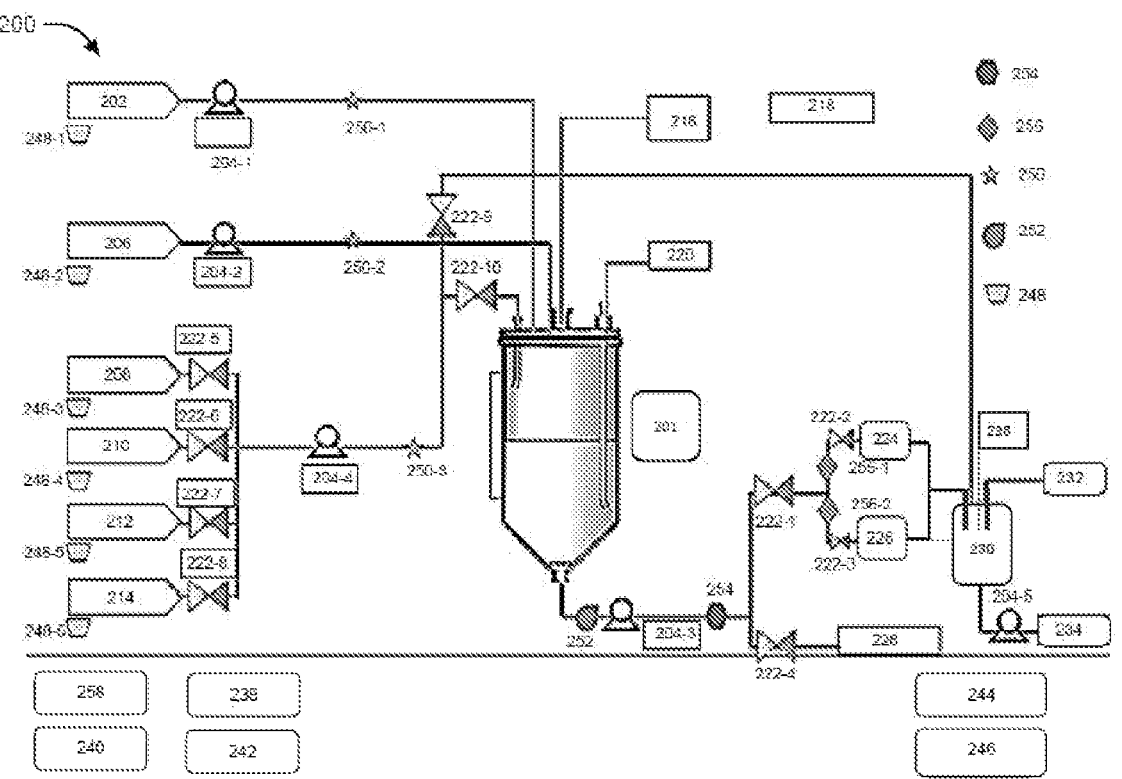
FIG. 4 is a schematic diagram showing the overview of viral inactivation system of the automated integrated continuous bioprocess system for manufacturing a therapeutic protein.

FIG. 4 illustrates an overview of the viral inactivation system in accordance with an embodiment of the present invention. The viral inactivation system (200) comprises a viral inactivation (VI) vessel (201) made of glass or stainless steel to collect the protein A elute coming from the first chromatography system. The VI vessel (201) contains overhead stirrer/magnetic stirrer (216) with multiple ports for addition and removal of elute. The viral inactivation system comprises of pH probe (220) connected to a transmitter for measuring the pH of the protein A elute received from the first chromatography system. The system further optionally comprises load cells (202), (206), (208), (210), (212), and (214) for holding various liquids like acid, base, NaOH, water, and buffers. The system further comprises 0.2-0.45 micron filters (224) and (226) to remove any precipitates that may have formed during the neutralization step. The system may optionally include flow sensors (250-1) to (250-3) to monitor flow of various liquids to VI vessel (201) and collection vessel (230). The system may also include level sensor(s) to check level of fluid in the VI vessel, and load cell sensors (248-1) to (248-6) to monitor the level of liquids in respective load cells. Provision for automatic switching of the fluid path between two filters, if one of the filters gets clogged during the continuous operations is provided in the control system, which may be pressure sensors based (256-1) and (256-2) or using toggle switch. The system may raise an alarm upon clogging and switching of the filters for operator intervention. The system may optionally also comprise of turbidity sensor (254) post inactivation vessel to measure the nephelometric turbidity unit (NTU). Upon crossing the threshold, the system will trigger an alarm for operator intervention. An optional air bubble sensor (252) attached in the fluid path post viral inactivation vessel can trigger the switching of fluid paths to prevent air bubble entering into the chromatography system. Air bubble trap (not shown) prevents air bubble entering into the chromatography systems. The viral inactivation (VI) vessel is specifically designed to allow addition of water, elute, acid, base and buffer(s) gently to avoid foaming & splashing of the fluids. The system consists of collection vessel (230), which is a vessel for collecting the post viral inactivated eluate. The collection vessel (230) contains overhead stirrer/magnetic stirrer (236) with multiple ports for addition and removal of various liquids and elute.

In an embodiment the viral inactivation system comprises various sensors to monitor and regulate the viral inactivation system in continuous and automated mode without interruption.

In an embodiment the viral inactivation system optionally comprises level or load cell sensors selected from but not limiting to (248-1) to monitor level of an acid, (248-2) to monitor level of a base, (248-3) to monitor level of a NaOH, (248-4) to monitor level of a water, (248-5) and (248-6) to monitor level of buffers.

In an embodiment the viral inactivation system optionally includes flow sensors to monitor flow of various liquids to VI vessel (201) and collection vessel (230), the flow sensors are selected from but not limiting to (250-1) to monitor flow of an acid, (250-2) to monitor flow of a base, and (250-3) to monitor flow of a NaOH, water, and buffers.

In an embodiment, the viral inactivation system is operably connected to a master controller such as PID, PLC or IPC for real time measurement and control of the pH. The control unit is programmable for multiple parameters for example pH set point, hold time, stirrer rpm, acid and base pump rate control, CIP cycle control. The viral inactivation system is controlled by various means selected from but not limiting to for various settings (238), for main electricity supply (240), for auto or manual mode selection (242), for alarm (244), for calibration (258), and for shutdown of the system (246). The controller signals various actuators such as valves (222-1) to (222-10) and pumps (204-1) to (204-5) in the system to regulate the flow of the liquid and also to control acid and base addition to the protein A elute for pH adjustment.

In an embodiment, the controller receives and sends signals from chromatography systems such as analog signals for example 0-10 V or 4-20 mA or digital signals from TTL logic or more advanced one or more interface(s) selected from but not limiting to OPC, modbus TCP/IP, EtherCAT, Profibus, Profinet, profibus, and industrial Ethernet. The signal from the first chromatography system triggers the viral inactivation program. The transmitter measures the signal generated by the pH probe (220) and transmits the values to the master controller. The system automatically adjusts the pH of the elute based on the set points in the controller, which activates the acid (202) or the base (206) addition followed by hold time for viral inactivation step. Upon completion of the viral inactivation hold time and adjusting of the pH for set point 2, the system pumps the elute post viral inactivation from the viral inactivation vessel (201) into the collection vessel (230). The fluid paths are controlled digitally by use of normally closed solenoid/pneumatic pinch valves (222-1) to (222-3), which block and divert the flow of fluid as required.

In an embodiment, upon transferring the protein A elute from viral inactivation vessel to collection vessel, the controller sends signals to the second chromatography system such as analog signals for example 0-10 V or 4-20 mA or digital signals from TTL logic or more advanced one or more digital interfaces selected from but not limiting to OPC, modbus TCP/IP, EtherCAT, Profibus, Profinet, profibus, and industrial ethernet. The trigger initiates loading of elute from collection vessel into the second chromatography system for further purification of Protein eluate A and provide purified protein.

In an embodiment, the controller initiates the CIP cycle in the viral inactivation vessel. In the VI vessel during the CIP cycle, controller signals pump (204-4) start and opens valve (222-5) for NaOH flow from the load cell (208). The flow of NaOH to the VI vessel is monitored through the flow sensor (250-3) and controlled by the pump (204-4). After set time adjusted with a hold time set means (218) for holding of NaOH in VI vessel has elapsed, the controller signals the waste pump (204-3) to remove the NaOH from VI vessel and triggers opening of a waste valve (222-4) for the waste outlet (228). Emptying of VI vessel of NaOH triggers air bubble sensor (252), which sends signal to the controller and stop the waste pump (204-3) and its valve (222-4), alternatively the controller can also be programmed to run the pump for set time until the vessel is emptied, if the air bubble sensor is not available. The controller then signals pump (204-4) to start and opens valve (222-6) to allow water to flow from load cell (210) and regulating the flow of water through valve (222-6), monitored by water sensor (250-3) and controlled by pump (204-4) to the VI vessel (201). After set time for holding of water in VI vessel has elapsed, the controller signals the waste pump (204-3) to remove the water from VI vessel and trigger opening of waste valve (222-4). Emptying VI vessel of water will trigger air bubble sensor (252), which sends signal to the controller and stop the waste pump (204-3) and its valve (222-4), alternatively the controller can also be programmed to run the pump for set time until the vessel is emptied, if the air bubble sensor is not available. The controller then signals pump to start and opens valve (222-7) to initiate flow of buffer from the load cell (212). The signal for emptying buffer from VI vessel and triggered by the first chromatography system once the protein elute A is ready to be loaded into the VI vessel. The controller accepts this signal and triggers the waste pump to remove the buffer from VI vessel and triggers opening of waste valve (222-4). Emptying VI vessel of buffer triggers air bubble sensor (252), which sends signal to the controller and stops the waste pump (204-3) and its valve (222-4), alternatively the controller can also be programmed to run the pump for set time until the vessel is emptied, if the air bubble sensor is not available.

Upon completion of the viral inactivation hold time and adjusting of the pH for set point 2, the system pumps the elute post viral inactivation from the viral inactivation vessel (201) into the collection vessel (230). The fluid paths are controlled digitally by use of normally closed solenoid/ pneumatic pinch valves (222-1) to (222-3), which block and divert the flow of fluid as required.

In an embodiment, post viral inactivation, the protein A elute from the VI vessel (201) through digitally controlled solenoid/pneumatic pinch valve (222-1), followed by another digitally controlled solenoid/pneumatic pinch valves (222-2) and/or (222-3) passes through 0.2-0.45 micron filters (224) and/or (226) to remove any precipitates that may have formed during the viral inactivation step. Optionally there may be provided a provision for pressure sensors (256-1) and (256-2) in the fluid path allows for automatic switching between two filters, if one of the filters gets clogged during the continuous operations. The system raises an alarm upon clogging and switching of the filters for operator intervention. Optionally there may be provided a provision for turbidity sensor (254) post inactivation vessel to measure the NTU upon crossing the threshold, the system will trigger an alarm for operator intervention. Optionally there may be a provision of air bubble sensor (252) post viral inactivation vessel triggers the switching off of fluid paths to prevent air bubble entering into the chromatography systems and air bubble trap prevents air bubble entering into the chromatography systems. Upon transferring of the viral inactivated and neutralized protein elute from VI vessel (201) after clarification through filters (224) and (226) to the collection vessel (230), the controller sends signals to the second chromatography system such as analog signals for example 0-10 V or 4-20 mA or digital signals from TTL logic or more advanced one or more digital interface(s) selected from but not limiting to OPC, modbus TCP/IP, EtherCAT, Profibus, Profinet, profibus, or industrial ethernet. The trigger initiates loading of protein elute from the collection vessel into the second chromatography system through port (232).

Figure 5:
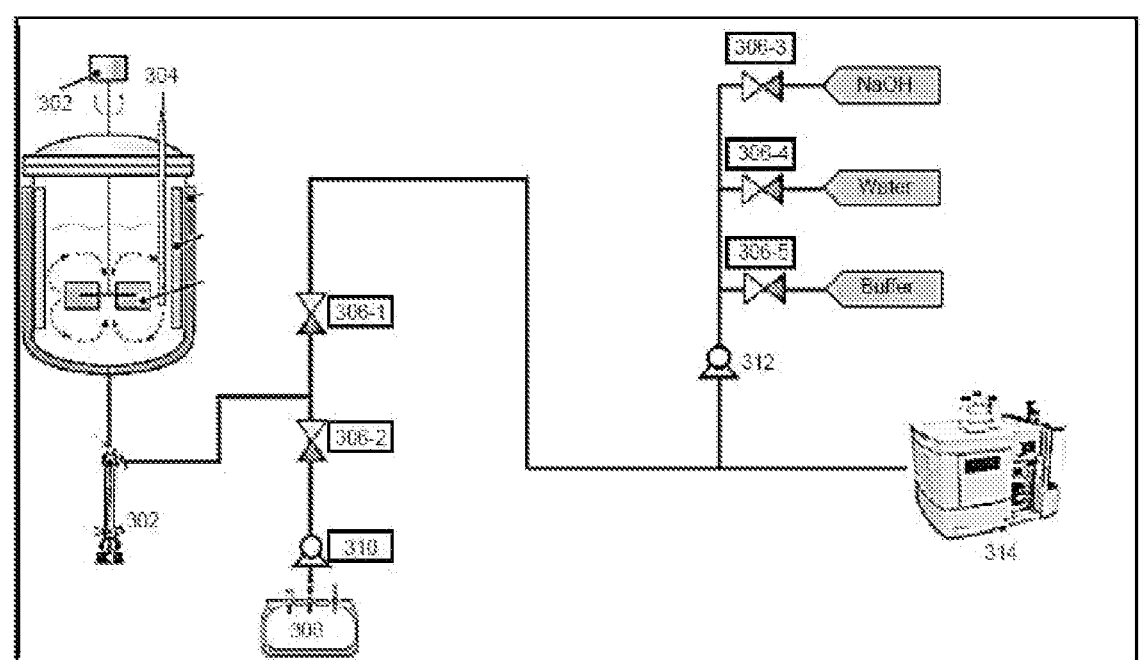
FIG. 5 is a schematic diagram showing the overview of CIP system of chromatography 1 of the automated integrated continuous bioprocess system for manufacturing a therapeutic protein.

FIG. 5 illustrates the overview of a cleaning in place (CIP) system for the first chromatography system, in accordance with an embodiment of the present invention. The CIP system (300) for the chromatography system is operably connected to the controller which signals various actuators such as valves and pumps in the system to regulate the flow of the fluid. The controller receives and sends signals from chromatography systems such as analog signals for example 0-10 V or 4-20 mA or digital signals from TTL logic or more advanced one or more digital interfaces selected from but not limiting to OPC, modbus TCP/IP, EtherCAT, Profibus, Profinet, profibus, and industrial ethernet. The signal from the first chromatography system (314) triggers the sample inlet CIP program. The controller opens bleed valve (306-2) to direct fluid/harvest to surge bag (308) and start the bleed pump (310). The controller opens CIP NaOH valve (306-3), starts pump (312) and simultaneously shuts down valve (306-1). After set time for NaOH flow through the first chromatography system has elapsed, the controller signals the NaOH valve (306-3) to shut down and simultaneously open water valve (306-4). After set time for water flow through the first chromatography system has elapsed, the controller signals the water valve (306-4) to shut down and simultaneously open buffer valve (306-5). After set time for buffer flow through the first chromatography system has elapsed, the controller signals the buffer valve (306-5) to shut down and bleed valve (306-2), pump (310), and valve (306-1) opens simultaneously thus achieving the cleaning in place of the first chromatography system during the process.

Further embodiments of the present disclosure relate to an automated integrated bio-manufacturing process that enables continuous production of a therapeutic protein in which the process is controlled with one or more control system selected from supervisory control and data acquisition (SCADA) control system (110), proportional integral derivative (PID), programmable logic circuit (PLC), industrial PC (IPC), Distributed control system (DCS), and message relaying system to run the process in an uninterrupted manner.

In an embodiment, the present invention relates to the automated integrated continuous bioprocess for producing therapeutic protein in an uninterrupted manner and scalable from laboratory to manufacturing scale of the present invention, comprises the steps of:

(a) culturing mammalian cells capable of producing a therapeutic protein in a liquid culture medium in a bioreactor (103) enabled with alternating tangential flow (ATF) filter (109) and collecting a bleeding harvest comprising protein secreted in the culture medium;

(b) feeding the cell culture harvest comprising the therapeutic protein from the bioreactor (103) into a first chromatography system (119) to provide a protein A elute;

(c) feeding the protein A eluate from the first chromatography system (119) into a viral inactivation vessel (128) and allowing inactivation of viruses that may be present in the protein A eluate;

(d) passing the virus inactivated, and neutralized protein A eluate through one or more filter(s) to remove impurities in the form of any precipitate formed during the viral inactivation and neutralization steps, and collecting a filtered protein A eluate in the collection vessel (136) and;

(e) feeding the neutralized and filtered protein A eluate to the second chromatography system (137) to provide further purified protein.

In an embodiment, the present invention provides the automated integrated continuous bioprocess, wherein mammalian cells are cultured in bioreactor (103), which is a perfusion bioreactor enabled with alternating tangential flow (ATF) technology.

In an embodiment, the present invention provides the automated integrated continuous bioprocess, wherein the clarified cell culture harvest is directly fed from bioreactor (103) into a first chromatography system (119) using the first chromatography system pump.

In an embodiment, the present invention provides the automated integrated continuous bioprocess, wherein the first chromatography step is carried out using one or more affinity chromatography column(s) for purifying the cell culture harvest comprising and the therapeutic protein from the bioreactor and providing a protein A elute.

In an embodiment, the present invention provides the automated integrated continuous bioprocess, wherein pH of the protein eluate A in the viral inactivation step is adjusted automatically by proportional-integral-derivative (PID) controller, programmable logic controller (PLC) or industrial personal computer (IPC) controller.

In an embodiment, the present invention provides the automated integrated continuous bioprocess, wherein in the second chromatography step is carried out using one or more multimodal anion exchange column(s), and one or more cation exchange column(s) to provide a purified protein.

In one embodiment, the present invention provides the automated integrated continuous bioprocess optionally further comprising storing the purified protein in an additional collection vessel (140) received from the second chromatography system (137). In one embodiment, the present invention provides the automated integrated continuous bioprocess optionally further comprising one or more steps of passing the purified protein through one or more filters (142) to further purify the therapeutic protein. The filter(s) can be selected from nanofilter, ultrafilter, and diafilter.

In an embodiment, the present invention provides the automated integrated continuous bioprocess, wherein the process includes automated sampling for online testing and cleaning in place using the (CIP) system (120) for periodic cleaning of chromatography system(s) and components thereof including chromatographic column(s), tubes, and vessels to maintain uninterrupted operation.

In an embodiment the bioprocess optionally comprises an automated HPLC sampling for online testing process parameters using supervisory control and data acquisition (SCADA) control system, cleaning in place (CIP) system and switching of the liquid flow path to maintain uninterrupted system operation. In an embodiment the bioprocess optionally further comprises automated UPLC sampling for online testing process parameters using supervisory control and data acquisition (SCADA) control system, cleaning in place (CIP) system and switching of the liquid flow path to maintain uninterrupted system operation.

In an embodiment, the integrated continuous bioprocess of the present invention can be controlled by a master controller consisting of IPC with SCADA software for control on visualization of the data, monitoring, and as an historian of the process parameters. The master controller capable of controlling individual systems such as bioreactor, first chromatography system, second chromatography system, and the virus inactivation system using one or more digital interfaces selected from but not limiting to OPC, modbus TCP/IP, EtherCAT, Profibus, Profinet, profibus, industrial ethernet ETC.

In another embodiment, the automated bioprocess of the present invention provides continuous transfer of product stream from an upstream process to downstream process.

In an embodiment the upstream process is carried out in a bioreactor of the automated integrated continuous bioprocess system with control systems suitable for culturing of mammalian cells. In an embodiment the upstream process is carried out in the bioreactor enabled using ATF technology, wherein a harvest comprising of a therapeutic protein produced is collected using HPLC system pump from ATF. The exemplary process flow for upstream process is shown in FIG. 1.

In an embodiment, the upstream process of culturing mammalian cell in the bioreactor adopts perfusion cell culture process and the culturing mammalian cell batch duration is selected from 3 to 16 days. Further, the upstream process can be carried out by culturing cells in different cell culture medium known to a person skilled in the art for the enhanced growth of the mammalian cell in the bioreactor.

Figure 2:
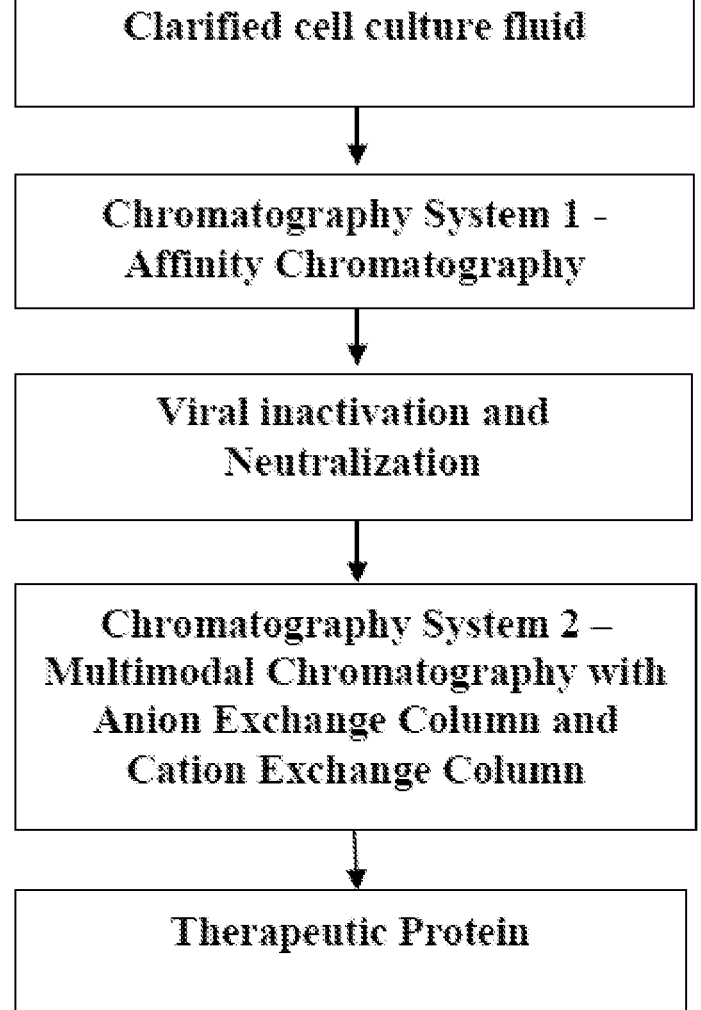
FIG. 2 illustrates an exemplary process flow for downstream process.

In an embodiment the downstream process comprises purification steps of the therapeutic protein produced during the upstream process in a continuous automated integrated bioprocess system, wherein the clarified cell culture fluid is fed into the first chromatography system comprising one or more affinity column(s) to provide a protein A eluate, inactivating and neutralizing the protein A eluate in a viral inactivation system and fed into a second chromatography system including one or more multimodal anion exchange chromatography column(s) and one or more cation exchange chromatography column(s) to provide a purified protein. The exemplary process flow for downstream process is shown in FIG. 2.

Different embodiments during upstream and downstream processes and operation of system of the present disclosure for producing protein of interest may employ cells selected from native, wild, mutated or genetically engineered cells capable of producing desired protein of an interest; nutrient or culture media suitable for the cells used; various chemicals; reagents; resins used during chromatography steps; and any suitable materials. In some embodiments different buffer (s) or buffer system(s) employed includes chemicals suitable as wash buffer, chase buffer, equilibration buffer, elution buffer or the like.

The automated integrated continuous system and bioprocess is capable of producing the therapeutic protein selected from an antibody, an antibody fragment, a monoclonal antibody, an enzyme, an engineered protein, an immunogenic protein, a protein fragment, an immunoglobulin or any combination thereof.

The therapeutic protein that prepared by the automated integrated continuous bioprocess in accordance with the present invention is selected from the group consisting of: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, amatuximab, anatumomab, anrukinzumab, apolizumab, arcitumomab, atinumab, tocilizumab, basilizimab, bectumomab, belimumab, bevacizumab, besilesomab, bezlotoxumab, biciromab, blinatumomab, canakinumab, certolizumab, cetuximab, cixutumumab, daclizumab, denosumab, eculizumab, edrecolomab, efalizumab, efungumab, epratuzumab, ertumaxomab, etaracizumab, figitumumab, golimumab, ibritumomab tiuxetan, igovomab, imgatuzumab, infliximab, inolimomab, inotuzumab, labetuzumab, lebrikizumab, moxetumomab, natalizumab, nivolumab, obinutuzumab, oregovomab, palivizumab, panitumumab, pertuzumab, ramucirumab, ranibizumab, rituximab, Secukinumab, tocilizumab, tositumomab, tralokinumab, tucotuzumab, trastuzumab, Ustekinumab, vedolizumab, veltuzumab, zalutumumab, zatuximab, enzymes, proteins, immunogenic or antigenic proteins or protein fragments, alglucosidase alfa, laronidase, abatacept, galsulfase, lutropin alfa, antihemophilic factor, agalsidase beta, interferon beta-1a, darbepoetin alfa, tenecteplase, etanercept, coagulation factor IX, follicle stimulating hormone, interferon beta-1a, imiglucerase, dornase alfa, epoetin alfa, insulin or insulin analogs, mecasermin, factor VIII, factor Vila, anti-thrombin III, protein C, human albumin, erythropoietin, granulocute colony stimulating factor, granulocyte macrophage colony stimulating factor, interleukin-11, laronidase, idursuphase, galsulphase, a-1-proteinase inhibitor, lactase, adenosine deaminase, tissue plasminogen activator, thyrotropin alpha, acid β-galactosidase, β-galactosi-
dase, neuraminidase, hexosaminidase A, and
hexosaminidase B.

While the foregoing describes various embodiments of
the disclosure, other and further embodiments of the disclo-
sure may be devised without departing from the basic scope
thereof. The scope of the invention is determined by the
claims that follow. The invention is not limited to the
described embodiments, versions or examples, which are
included to enable a person having ordinary skill in the art
to make and use the invention when combined with infor-
mation and knowledge available to the person having ordi-
nary skill in the art.

EXAMPLES

The present invention is further explained in the form of
following examples. However, it is to be understood that the
following examples are merely illustrative and are not to be
taken as limitations upon the scope of the invention.

Example 1

Production and Purification of Cetuximab with the Auto-
mated Integrated Continuous System and Bioprocess
Upstream Process—Production of Protein For producing protein of interest the cell line used in the
automated continuous process was CHO-S Cell Line with a
Catalog Number of 11619012 procured from INVITRO-
GEN, USA.

Before inoculation of CHO mammalian cells, dissolved
oxygen (DO) calibration is carried out by sparging 0.5 LPM
of air. Once the DO value is stabilized then the DO probe is
calibrated to 100%.

For the continuous process ATF was used, which is a
filtration and perfusion system in which an alternating
tangential flow through a filter cartridge is used to establish
a highly efficient filtering. This allows the growth of cells up
to densities of 80-100 million cells per millilitre with a
viability of over 90%, resulting in extremely high yield of
protein.

The bioreactor was filled to its working volume with
culture media such as ActiPro and then inoculated with
mammalian cells i.e. CHO cells, 0.3-0.5×10⁶ viable mam-
malian cells/mL. A culture was run for 3 days. The alter-
nating tangential flow (ATF) System was then started and
within 5-10 minutes the reactor and the ATF were in fast
equilibrium. In an alternating tangential flow through a filter
cartridge is used to establish a highly efficient filtering. This
allowed the growth of cells up to densities of 80-100 million
cells per millilitre with a viability of over 90%, resulting in
extremely high yield of protein. Cells were pumped in and
out of the hollow fiber into reactor with a recirculation rate of 1.5-6 L/min depending on cell concentration. The filtrate
pump connected to AKTA™ periodic counter-current chro-
matography (PCC) was then started. The media used from
day 3-16 for perfusion was PM-Basal media+cell boost 7a (1
g/L) and cell Boost (1 g/L)+8 g/L Glucose and 8 mM
Glutamine.

The filtrate rate was started at 0.25 reactor volume (RV)
on day 3, 0.5 RV on day 4, 1 RV from day 5-7, 1.25RV from
day 8-9 and 1.5RV from day 10-16. It was ensured that the
pump made a tight enough seal to ascertain that the vacuum
on the filtrate side is maintained (which is the transmem-
brane pressure). This is because the ATF exerts a back flush
on each cycle that pulls a small amount of liquid from the
filtrate back across the filter into the reactor. As the ATF
system does not control the pump flow rate—it was con-
trolled manually by the user by controlling the flow rate of
the HPLC system pump.

Cell growth and cell viability were monitored daily
throughout the cultures. Cell growth profile is provided in
the table-1

TABLE 1

| Culture Age (Days) | VCC (mill/mL) | Viability (%) |
|---|---|---|
| 0.0 | 0.58 | 99.0 |
| 1.0 | 0.89 | 99.2 |
| 2.0 | 1.8 | 99.7 |
| 3.0 | 2.7 | 98.5 |
| 4.0 | 4.8 | 98.1 |
| 5.0 | 11.4 | 99.2 |
| 6.0 | 29.6 | 99.0 |
| 7.0 | 47.8 | 98.8 |
| 8.0 | 59.5 | 98.2 |
| 9.0 | 68.0 | 98.2 |
| 10.0 | 78.0 | 97.5 |
| 11.0 | 85.0 | 98.1 |
| 12.0 | 88.0 | 96.8 |
| 13.0 | 92.0 | 95.2 |
| 14.0 | 100.0 | 95.0 |
| 15.0 | 94.3 | 93.2 |
| 16.0 | 92.3 | 90.0 |

Data in the table above clearly indicates that cell viabili-
ties were maintained at acceptable values (>90%) through-
out the cultures in the established culture conditions.

Figure 6:
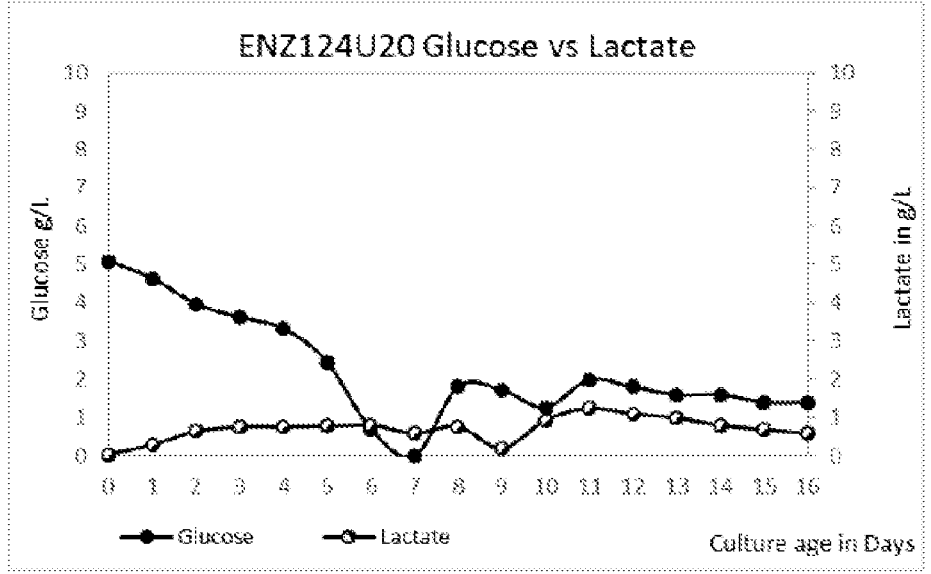
FIG. 6 is a graph showing the effect of lactose Vs glucose in cell growth on different days.

The effect of cell culture medium on cell growth was also
studied. Results of cell growth using glucose and lactate as
cell culture mediums are shown in FIG. 6.

Downstream Process: Purification of the Protein Produced

A. Chromatography 1ˢᵗ step was carried out using affinity
chromatography system with 4 columns, with the following
process parameters of the downstream processing as pro-
vided in the Table 2(a).

TABLE 2(a)

| Process Step | Process Parameters |
|---|---|
| Affinity Chromatography | Affinity Chromatography: Columns used: 4 columns Column diameter: 5 cm Resin: Mab Select Sure LX Bed height: 8.6 ± 0.2 cm Bed volume: ~168 mL Residence time: ~4 min Operational flow rate: 42 mL/min Equilibration Buffer: 50 mM Sodium phosphate buffer, pH 7.0 Wash 2 Buffer: 50 mM Sodium phosphate buffer + 1M NaCl, pH 7.0 |

TABLE 2(a)-continued

| Process Step | Process Parameters |
|---|---|
| | Wash 3 Buffer: 50 mM Sodium acetate buffer, pH 5.5<br>Elution buffer: 200 mM Acetic acid<br>Regeneration and sanitization solution: 100 mM sodium<br>hydroxide solution<br>Column storage solution: 20% Ethanol or 2% benzyl alcohol.<br>Load factor: ~35 mg/mL<br>Elution: Step elution with elution buffer.<br>Elution collection: For 2 mm path length of UV flow cell<br>collect elute fraction from 50 mAU in ascending side till three<br>column volumes of protein A column (168 mL × 3) mL. |

The first chromatography system was connected with four columns to four different column positions of AKTA PCC system and ~3 CVs of Milli Q water was passed through the columns to remove storage solution.

Column Equilibration: The first chromatography system equilibration buffer container was connected to the system and set-mark of "Equilibration" was given. All the columns were equilibrated by passing 3 CV's of buffer.

Loading: S1 line of the first chromatography system, AKTA PCC was connected to the ATF outlet and loading was started through it. Set-mark of "Loading" and "Auto-zero UV" command was given to it. 1st cycle loading on first column was done for 219 min.

Post load equilibration buffer wash: After loading for 219 min (1 cycle), the process was switched from loading step to washing step by diverting flow to Chromatography-1 buffer Regeneration: Post elution the column was regenerated by passing regeneration buffer for 3 CV's.

Milli Q water wash: Passed 3 CV's of Milli Q water to remove the sanitization solution.

Equilibration Buffer: Passed 3 CV's of EQB to re-equilibrate the column after regeneration.

Storage of column: Passed 2 CV's of chromatography-1 storage solution for storage of column (after end of all the cycles).

B. In an alternate process, downstream processing was carried out using affinity chromatography system with two columns to reduce the resin utilization per batch. The processes parameters followed were as per Table 2(b):

TABLE 2(b)

| Process Step | Process Parameters |
|---|---|
| Affinity<br>Chromatography | Affinity Chromatography:<br>Columns Used: Two<br>Column diameter: 5 cm<br>Resin: Mab Select Sure LX<br>Bed height: 4.2 ± 0.2 cm<br>Bed volume: ~84 mL<br>Residence time: ~2 min<br>Operational flow rate: 42 mL/min<br>Equilibration Buffer: 50 mM Sodium phosphate buffer, pH<br>7.0<br>Wash 2 Buffer: 50 mM Sodium phosphate buffer + 1M NaCl,<br>pH 7.0<br>Wash 3 Buffer: 50 mM Sodium acetate buffer, pH 5.5<br>Elution buffer: 200 mM Acetic acid<br>Regeneration and sanitization solution: 100 mM sodium<br>hydroxide solution<br>Column storage solution: 20% Ethanol or 2% benzyl<br>alcohol.<br>Load factor: ~35 mg/mL<br>Elution: Step elution with elution buffer.<br>Elution collection: For 2 mm path length of UV flow cell,<br>collected elute fraction from 50 mAU in ascending side till<br>three column volumes of protein A column (294 mL × 3) mL. | through the different pump of AKTA PCC system. Set-mark of "Post Load Equilibration Buffer Wash" was given and 3 CV of buffer was passed through the column.

When process step was switched from loading step to washing step in this cycle, loading step started on another column simultaneously as a different cycle.

Intermediate wash 2: After post load wash, 2 CV's of wash 2 buffer was passed through the column.

Wash 3: After wash 2 buffer wash, 2 CV's of wash 2 buffer was passed through the column.

Elution: Desired protein was eluted by chromatography-1 elution buffer. The elution peak was collected from 150 mAU till 3 CV's as total elution volume.

Figure 7:
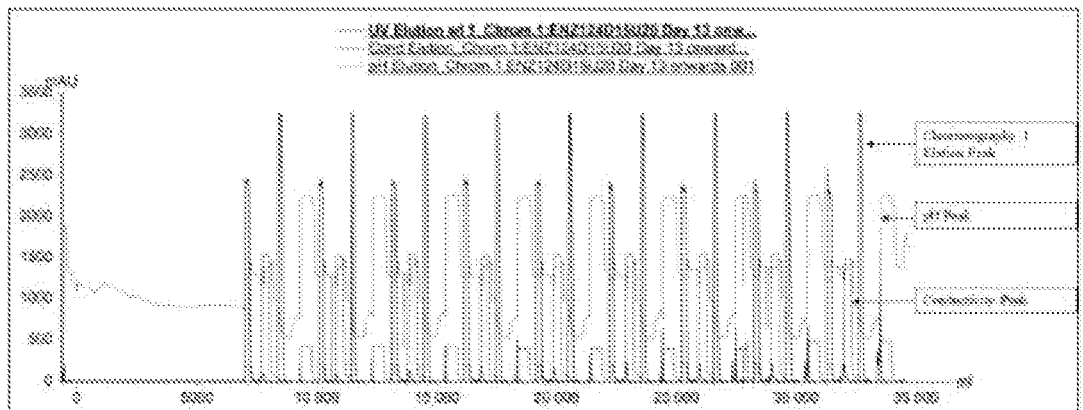
FIG. 7 is a chromatogram profile of chromatography system 1 showing pH peak, elute peak and conductivity peak.

Thus, as a result of chromatography $1^{st}$ step carried out with an affinity chromatography using Mab Select Sure LX resin capturing protein of interest, the protein of interest was bound to the resin and the impurities were removed as flow through. Chromatogram obtained in this step is shown in FIG. 7, which shows elution peak corresponding to the contained protein of interest eluted using low pH buffer (pH ~2.8), the elution peak was observed consistently as expected for all the cycles.

Low pH Viral Inactivation Treatment and Neutralization

Viral inactivation and neutralization was carried out using following parameters as per Table 3:

TABLE 3

| Low pH viral inactivation | Low pH inactivation: Inactivation pH: 3.5 ± 0.2 Incubation time: 45 min ± 5 Temperature: RT (23 ± 2)° C. Neutralization buffer: 2M Tris base Neutralization pH: 5.5 ± 0.2 |
|---|---|

The pH of protein A eluate of each cycle was maintained in the expected range of 3.5±0.2 after mixing (control system ensures this range through feedback mechanism). After considering the pH, the complete mixing of protein solution for 45±5 min at room temperature (23±2° C.) was made and noted down the incubation start time, end time, incubation duration and temperature.

After 45±5 min of incubation, the pH of protein solution was adjusted to 5.5±0.2 with 2 M Tris base solution by control system based on feedback mechanism. Conductivity after neutralization is expected to be ~6 mS/cm. Post neutralization, the protein solution was passed through the Sartopore® capsule 0.2 μm filter by peristaltic pump driven by control system and the filtrate was collected in the second collection vessel for further processing for multimodal and cation exchange chromatography step.

Multimodal Anion Exchange Chromatography and Cation Exchange Chromatography

Protein was purified using second chromatography system using multimodal anion exchange chromatography and cation exchange chromatography with following parameters as per Table 4:

The first column that is anion exchange column of the second chromatography system was connected to the versatile valve position of 2 & 4 of AKTA pure system and the second column that is cation exchange column of the second chromatography system was connected to the column position 1. 3 CV's of Milli Q water was passed through the columns to remove storage solution.

High salt wash buffer: 2 CV's of high salt wash buffer was passed through anion exchange and cation exchange columns of the second chromatography system and ensured the pH and conductivity of columns were in the range of high salt wash buffer.

Column equilibration: Both the columns were equilibrated by passing 5 CVs of equilibration buffer.

Loading and buffer chase: The neutralized and filtered protein A elute sample collected in collection vessel was loaded through the columns connected in series where the protein of interest didn't bind to the anion exchange column of the second chromatography system and passed as flow through and it bound to the cation exchange column of the second chromatography system. After loading was over, 100 mL equilibration buffer was dispensed to the load container and it was passed through the columns to ensure complete loading of the neutralized protein eluate sample.

Post load equilibration buffer wash: After equilibration buffer chase, another 2 CV's of equilibration buffer was passed as the peak of the anion exchange column of the second chromatography system flow through steadily stabilized and to remove loosely bound and unbound protein on the cation exchange column of the second chromatography system. Protein of interest bound to the cation exchange

TABLE 4

| Anion and Cation Exchange Chromatography | Anion exchange chromatography: Column diameter: 2.6 cm Resin: Capto adhere ImpRes Bed height: ~15 ± 0.2 cm Bed volume: ~80 mL Residence time: ~4 min Operational flow rate: 20 mL/min High salt wash buffer: 50 mM sodium phosphate buffer + 300 mM sodium chloride pH 5.5 Equilibration Buffer: 50 mM Sodium Phosphate, pH 5.5 Regeneration and sanitization solution: 1M sodium hydroxide + 2M sodium chloride. Column storage solution: 10 mM sodium hydroxide solution Load factor: ~50 mg/mL Elution: Flow through (Negative) mode Peak collection: Protein in flow through directly binds to CEX column connected in series. Cation exchange chromatography: Column diameter: 3.2 cm Resin: SP Sepharose FF Bed height: 20 cm ± 0.5 cm Bed volume: ~160 mL Residence time: ~8 min Operational flow rate: 20 mL/min for loading and post load wash and 32 mL/min during subsequent operation Equilibration Buffer: 50 mM Sodium acetate buffer, pH 5.5 Elution Buffer: 50 mM Sodium acetate buffer + 150 mM Sodium Chloride, pH 5.5 Regeneration and sanitization solution: 1000 mM sodium hydroxide + 2000 mM sodium chloride. High salt wash buffer: 20 mM sodium acetate buffer + 300 mM sodium chloride pH 5.5 Column storage solution: 10 mM sodium hydroxide Load factor: ~25 mg/mL Elution: Step elution Elution collection: For 2 mm path length of UV flow cell, collected elute fraction from 50 mAU in ascending side to 50 mAU on descending side. |
|---|---| column of the second chromatography system was then eluted using cation exchange chromatography elution buffer. The elution peak was collected from 150 mAU of peak to 150 mAU of peak at UV280 nm for 2 mm path length of flow cell. The elute fraction of each cycle was stored at 2 to 8° C. till further processing.

Regeneration: 2 CV's of anion exchange and cation exchange chromatography regeneration buffer was passed through both the columns.

Milli Q water wash: 2 CV's of Milli Q water was passed to remove the regeneration solution.

Storage of column: 2 CV's of anion exchange and cation exchange storage solution was passed for storage of columns (at the end of all the cycles).

Figure 8:
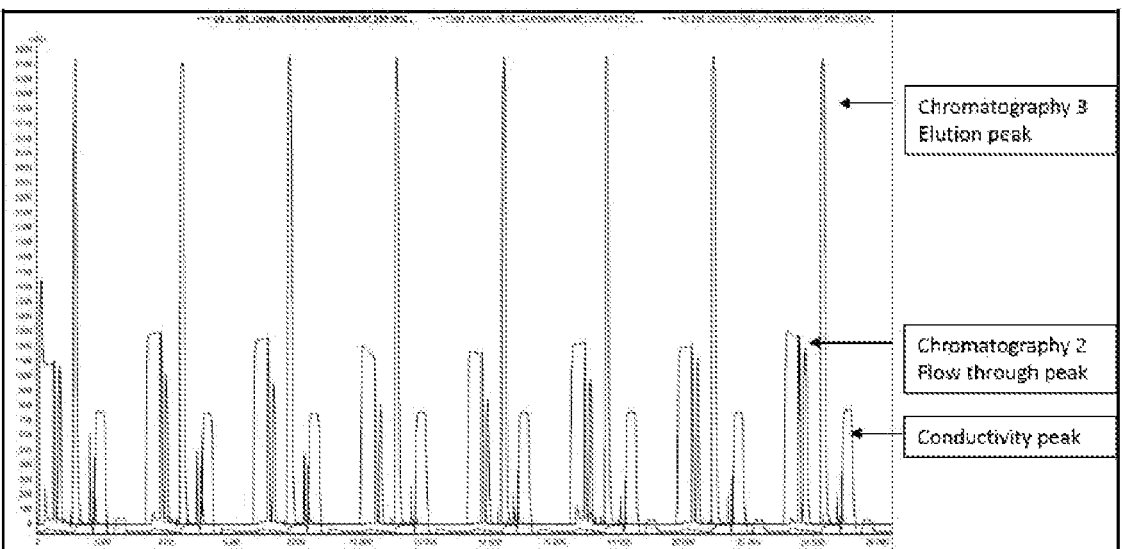
FIG. 8 is a chromatogram profile of chromatography system 2 showing elution peak, flow through peak and conductivity peak.

Thus, chromatography step 2, comprised of two stages, first a multimodal anion exchange chromatography where Capto Adhere Impres resin was used and second stage of a cation exchange chromatography where SP sepharose FF resin was used. After the multimodal anion exchange chromatography, impurities were bound to the column and protein of interest passed as flow through. The cation exchange chromatography column was connected to the anion exchange chromatography column in tandem, where the protein of interest was bound to it. Protein was then eluted from the cation exchange chromatography column using high salt buffer. Chromatogram obtained in this step is shown in FIG. 8, in which elution peak can be observed consistently for all the cycles as expected.

Tangential Flow Filtration (Ultrafiltration and Diafiltration)

The eluate from the cation exchange chromatography was pooled and processed further for tangential flow filtration to concentrate and buffer exchange the cetuximab protein into formulation buffer without the final excipient as per the parameters shown in Table 5 as below:

TABLE 5

| TFF system | Cogent μ scale |
|---|---|
| Cassette | Pellicon Biomax 30 |
| Cassette area | 0.1 m$^2$ |
| Cassette MOC | PES |
| Concentration of chromatography 3 eluate | Upto 50 mg/mL |
| Buffer exchange | 8 Diafiltration volumes |
| Pressure | ≤1 bar |
| Cut off size/MWCO | 30 kDa |

The protein solution recovered from the TFF system was diluted to 5 mg/mL using formulation buffer with final excipient solution.

The resultant solution was filtered through 0.2 μm filter (MOC-Polythersulfone) aseptically into a PETG bottle. The filtrate thus obtained was the final protein product cetuximab suitable for use as drug substance.

The recovery data of the exemplary representative batch was observed as per Table 6 as follows:

TABLE 6

| Step | Total protein (mg) | Recovery (%) |
|---|---|---|
| Chromatography 1 load | 30240 | 82 |
| Chromatography 3 elute pool | 24816 | |
| TFF load | 24816 | 97.9 |
| TFF retentate | 24300 | |
| Drug substance | 24300 | 100 |
| Overall Yield | | 80.35% |

The foregoing examples are merely illustrative and are not to be taken as limitations upon the scope of the invention. Various changes and modifications to the disclosed embodiments will be apparent to those skilled in the art. Such changes and modifications may be made without departing from the scope of the invention.

Advantages of the Present Invention

The present invention provides an automated bioprocess for sustained operation for continuous process for multiple days without repeated changing of the vessels/bags during the process.

The present invention provides an automated integrated continuous bioprocess system which uses controller to regulate and monitor the entire upstream and downstream process using SCADA or DCS.

The present invention provides an automated integrated continuous bioprocess system for producing therapeutic protein which comprises of a scalable and accurate real time automated pH adjustment system for viral inactivation The present invention provides an automated bioprocess and system wherein the automated online sampling for HPLC analysis allows in depth process analytics as well as feedback for process parameters.

The present invention provides an automated integrated continuous bioprocess for producing therapeutic protein using system comprising pinch valves for trouble free replacement of tubing after every continuous batch completion resulting in ease of operations.

We claim:

1. An automated integrated continuous bioprocess system (100) for producing therapeutic protein comprising:

a bioreactor (103) to culture mammalian cells capable of producing the therapeutic protein in culture medium, the bioreactor (103) comprises alternating tangential flow (ATF) filter (109) to collect a harvest comprising the therapeutic protein secreted into the culture medium;

a first chromatography system (119) comprising one or more affinity chromatography column(s) connected to the ATF filter (109) without any intermediate hold vessel to purify the harvest comprising the therapeutic protein and provide protein A eluate;

a viral inactivation system (126) including a viral inactivation vessel (128) with a pH probe connected to a transmitter for measuring the pH of the protein A elute connected to the first chromatography system (119) to collect the protein A eluate and inactivate viruses that may be present in the protein A eluate, and the viral inactivation vessel (128) configured to automatically adjust pH of the protein A eluate to obtain a virus inactivated, neutralized, and filtered protein A eluate;

a collection vessel (136) connected with the viral inactivation vessel (128) through one or more filters to receive the virus inactivated, neutralized, and filtered protein A eluate, wherein said one or more filter(s) (224) and (226) are configured to remove impurities as precipitates from the virus inactivated, neutralized, and filtered protein A eluate received from the viral inactivation vessel;

a second chromatography system (137) comprising one or more multimodal anion exchange column(s) and one or more cation exchange column(s) connected with the collection vessel (136) to receive the virus inactivated, neutralized, and filtered protein A eluate from the collection vessel (136) and to provide purified protein;

one or more of solenoid or pneumatic pinch valves (114), sensors, air bubble sensors, pressure sensors and load cell sensors for creating a feedback loop in order to maintain fluid flow using tubes between various components of the system, avoid formation of air bubbles and regulate flow of liquid;

cleaning in place (CIP) system (120) comprising a plurality of reservoirs of cleaning solutions and a plurality of valves for periodic cleaning of the first chromatography system and/or second chromatography system, viral inactivation vessel, collection vessel, and tubes;

one or more control systems selected from supervisory control and data acquisition (SCADA) control system (110), proportional integral derivative (PID); programmable logic circuit (PLC), Industrial PC (IPC), distributed control system (DCS); Input-Output Modules or IO Boxes (130) and (132) operably connected with the first chromatography system (119); the viral inactivating system (126); the collection vessel (136); and the second chromatography system (137).

2. The automated integrated continuous bioprocess system as claimed in claim 1, further comprising a surge bag (116) connected with the bioreactor through a valve (114).

3. The automated integrated continuous bioprocess system as claimed in claim 1, wherein the viral inactivation system (126) comprises a viral inactivation (VI) vessel (128), a pH probe (220) connected to a transmitter for measuring the pH of the protein A eluate, autotitrator (122), load cell sensors (248-1, 248-2, 248-3, 248-4, 248-5, and 248-6) to monitor the level of liquids in respective load cells, a level sensor to check level of fluid in the VI vessel, pressure sensors (256-1) and (256-2) in the fluid path, inline turbidity measuring sensor (254) to measure real time turbidity, and an air bubble sensor (252) to prevent air bubble entering into the first chromatography system and/or second chromatography system.

4. The automated integrated continuous bioprocess system as claimed in claim 1, wherein each of the filters between viral inactivation vessel and the collecting vessel is 0.2-0.45 micron filter.

5. The automated integrated continuous bioprocess system as claimed in claim 1, wherein the viral inactivation vessel, and the collection vessel are made of glass or stainless steel.

6. The automated integrated continuous bioprocess system as claimed in claim 1, wherein the cleaning in place (CIP) system (120) for periodic cleaning of the first chromatography system and/or second chromatography system includes cleaning of components thereof including chromatographic column(s), and inlet.

7. The automated integrated continuous bioprocess system as claimed in claim 1, further comprises an automated harvest sampling from bioreactor for cell count and nutrient analysis, and automated sampling at different locations for online chromatography analysis in the automated integrated continuous bioprocess.

* * * * *